United States Patent [19]
Nicholls

[11] Patent Number: 5,129,267
[45] Date of Patent: Jul. 14, 1992

[54] FLOW LINE SAMPLER

[75] Inventor: Colin I. Nicholls, San Antonio, Tex.

[73] Assignee: Southwest Research Institute, San Antonio, Tex.

[21] Appl. No.: 486,907

[22] Filed: Mar. 1, 1990

[51] Int. Cl.$^5$ .............................................. G01N 1/14
[52] U.S. Cl. ................................. 73/863.84; 324/321
[58] Field of Search ............... 324/300, 306, 307, 318, 324/321; 73/863.71, 863.83, 863.84, 864.62

[56] References Cited

U.S. PATENT DOCUMENTS

| | | | |
|---|---|---|---|
| 3,184,973 | 5/1965 | Bradley | 73/422 |
| 3,282,113 | 11/1966 | Sachnik | 73/863.84 |
| 3,726,143 | 4/1973 | Enarsson | 73/422 |
| 4,147,062 | 4/1979 | Jaeger | 73/422 |
| 4,307,620 | 12/1981 | Jiskoot | 73/863.61 |
| 4,390,957 | 6/1983 | Skarlos et al. | 324/300 |
| 4,820,990 | 4/1989 | Moore | 73/864.35 |

Primary Examiner—Hezron E. Williams
Assistant Examiner—Louis M. Arana
Attorney, Agent, or Firm—Baker & Botts

[57] ABSTRACT

An on-line product sampling apparatus and method for measuring product samples from a product stream (12) in a flow line (14) having a sampling aperture (11), includes a sampling tube (18) for containing product samples removed from flow line (14). A piston (22) removes product samples from the product stream (12) through the sampling aperture (11) and returns samples to product stream (12). A sensor (20) communicates with sample tube (18), and senses physical properties of samples while the samples are within sample tube (18). In one embodiment, sensor (20) comprises a hydrogen transient nuclear magnetic resonance sensor for measuring physical properties of hydrogen molecules.

9 Claims, 3 Drawing Sheets

FLOW LINE SAMPLER

NOTICE

The U.S. Government has a paid-up license in this invention and the right in limited circumstances to require the patent owner to license others on reasonable terms as provided for by the terms of Project No. 15-2236 for the Department of Energy (D.O.E.).

BACKGROUND OF THE INVENTION

This invention generally relates to an apparatus for measuring physical properties of fluids and more particularly to a simplified product sampling apparatus for making on-line measurements of flowing materials.

In production processes, it is often desirable to measure physical properties of products that flow through some sort of flow line as they are flowing. For example, in the production of wet corn milling, there is a need for an apparatus to provide moisture content measurement. Such a mechanism must be sufficiently robust to withstand a variety of harsh industrial environments. With an apparatus of this type, the corn milling industry, for example, could generate a substantial savings in industrial energy consumption because corn drying processes could be programmed to terminate at precisely the desired dryness level. Other examples of industries requiring flow line measurement systems having high reliability, low operating costs, and economical implementation are those producing food, lumber, textiles, agricultural products, tobacco, coal, and paper.

In broader applications, not necessarily directed to flow line measurements, various means for obtaining liquid samples have developed. Existing devices for liquid sampling fall in two broad categories. The first category includes devices that simply provide a means for extracting the desired product samples. The sensing or measuring devices that are to be used for product analysis are typically physically and mechanically separate from the on-line system. The other category of devices are used in systems having a sensor downstream of a point at which the sample is diverted from a flow line. Sensors for both categories of sampling systems could include a wide array of non-intrusive testing techniques, including means for measuring low resolution nuclear magnetic resonance, electrical resistivity, density, and dielectric constant, for example.

For example, U.S. Pat. No. 4,744,255 issued on May 17, 1988 to Jaeger typifies the first category of product sampling systems. That disclosure shows a product sampling apparatus for communicating with the interior of a vessel containing a liquid. The product sampling apparatus extracts a liquid sample of predetermined volume from the vessel and conveys the sample to a point of collection. The invention is directed to a device for collecting a number of samples over time and combining them to obtain a composite. A plunger having a product-containing recess is used to convey the samples to a larger collection tank, so that desired measurements can be made. A limitation of this type of device is that such devices do not permit "instantaneous" sample-and-measure techniques. Also, the samples are not returned to the flow line. If the product requires a special environment, the device would not maintain those conditions, so as to permit returning the sample to the flow line in the same condition.

Using a thief product stream to divert part of the main product stream to a sensor exemplifies the second category of product sampling apparatus. Although these devices are "on-line" in the sense that the product can be measured as it flows, a disadvantage of this approach is that the product in the thief stream may not have the same characteristics as the product in the product stream. Also, a thief product stream poses potential problems related to achieving a product stream flow through the comparatively smaller thief product stream pipe. By the time the product is diverted and measured, the measurements thus obtained may not be real-time representations of the product flow.

There is a need for an on-line sampling apparatus that permits real-time measurements. The device should be sufficiently rugged for an industrial production process environment, have low-maintenance and operating costs and capable of being readily interfaced to the control processes of an industrial plant.

SUMMARY OF THE INVENTION

The present invention provides an on-line product sampling apparatus that satisfies the aforementioned needs. A first aspect of the invention is an apparatus for measuring product samples from a product stream flowing in a flow line. The invention is comprised of a housing, a sample tube, a means for providing fluid communication between the flow line and sample tube, a sensor, a piston, and an actuator.

Generally, the present invention comprises an on-line product sampling apparatus for measuring product samples from a product stream in a flow line having a sampling aperture. The apparatus includes a sampling tube, which contains product samples that a piston removes from the flow line via the aperture. The piston cycles through a sample-return cycle, during which it removes a product sample from the product stream and returns the sample to the product stream. A sensor senses physical properties of the removed product samples during the time they are within the sample tube and during the piston cycle.

Another aspect of the invention is a method for making measurements of product samples from a product stream flowing in a flow line having a sampling aperture. The method comprises the steps of removing at least one product sample from the flow line through the sampling aperture, containing removed product samples within a sample tube that is integrally connected to the flow line at the sampling aperture, sensing physical properties of removed product samples while the product samples are stationary within the sample tube, and returning product samples to the flow line through the sampling aperture after sensing product sample physical properties.

An advantage of the invention is that it provides an on-line product sampling system in which the sample is extracted from the product stream, measured, and then returned to the product stream. The invention may operate in a series of sample-measure-return cycles and thereby provide real-time or near real-time measurements of flowing product. The return step eliminates product wastage. The invention provides a product sampling apparatus that is much simplified over known systems since it requires no valves or controls other than a piston. Another advantage of the apparatus of the present invention is that the only modification that it requires of the flow line is the cutting of one hole. Yet another advantage of the present invention is that it can be made very compact, thereby permitting flexibility in locating the product sampling apparatus in places on the flow line where known devices cannot be placed. Still another advantage of the present invention is that, because of its simplicity, it can easily be made sufficiently rugged to withstand a harsh industrial environment.

BRIEF DESCRIPTION OF THE DRAWINGS

The novel features believed characteristic of the invention are set forth in the appended claims. The invention itself, however, as well as modes of use and further advantages, is best understood by reference to the following description of illustrative embodiments when read in conjunction with the accompanying drawings.

DETAILED DESCRIPTION OF THE INVENTION

Figure 1:
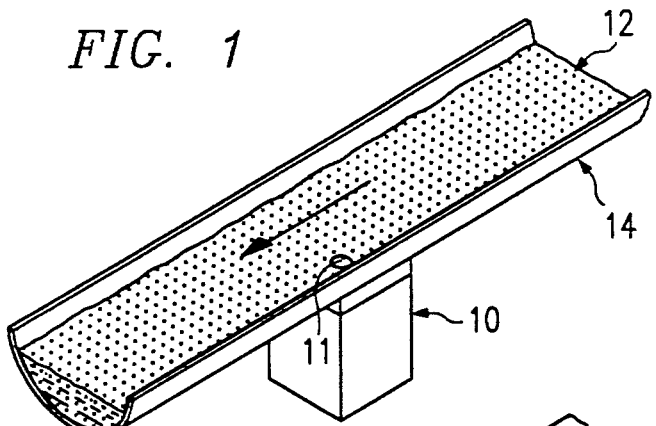
FIG. 1 is an enlarged perspective view of a preferred embodiment of the on-line product sampling apparatus with the sample tube filled with product for sample measurements.

FIG. 1 is a perspective view of the invention, a flow line sampler 10 for obtaining samples from flowing product stream 12 in a flow line 14 and enabling various measurements. This system will permit measurements on solid, liquid or gaseous flows. Although FIG. 1 shows flow line 14 as an open chute, it could be any type of flow line, especially including a pipe. As shown in FIG. 1, sampler 10 is essentially non-intrusive, requiring only a hole, depicted as sampling aperture 11, in the flow line 14.

Sampling aperture 11 provides a means for fluid communication between flow line 14 and sampler 10. In a preferred embodiment, sampling aperture 11 comprises a small opening of approximately one and one-half inches (1.5") in diameter placed in flow line 14. No thief product stream or major re-plumbing is necessary, as is the case with known product sampling apparatuses. As explained below, the invention does not require special valves or controls, or other retrofitting other than aperture 11.

Figure 2:
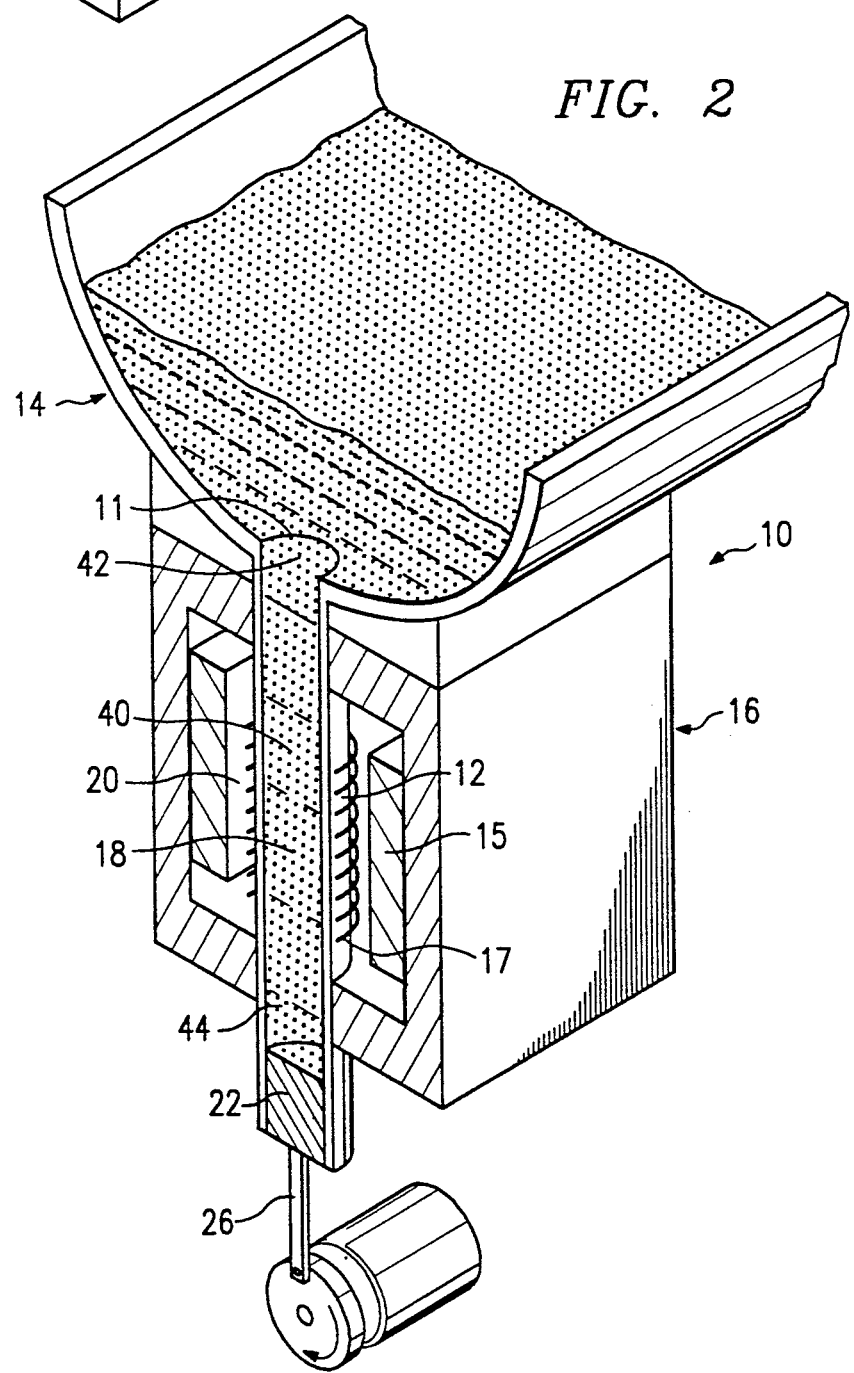
FIG. 2 is a side elevational view of the apparatus connected to a flow line as it would appear in operation.

FIG. 2 is a cross-sectional view of sampler 10, which has five basic elements: housing 16, sample tube 18, sensor 20, piston 22 and actuator 26. FIG. 2 uses as an example for sensor 20 a hydrogen transient nuclear magnetic resonance (HTNMR) measuring device. The depiction of sensor 20 as a HTNMR sensor, however, is for illustrative purposes, for, as explained below, sensor 20 may be any one of a number of sensing devices.

Housing 16 is fixedly mounted to flow line 14 at sampling aperture 11. Housing 16 can be any shape or size, consistent with its primary function, which is to house sensor 20. The configuration of housing 16 may depend on particular characteristics of sensor 20, such as whether or not the sensing method that sensor 20 employs requires physical contact between sensor 20 and sampling tube 18.

Sample tube 18 has a port end 42 and a stopper end 44. Port end 42 connects to sampling aperture 11 to receive product samples from flow line 14. In a preferred embodiment, sample tube 18 mounts orthogonally to flow line 14 and creates a leak-proof seal between flow line 14 and sample tube 18 at sampling aperture 11. Sample tube 18 provides a means for containing product samples removed through sampling aperture 11 as they are sensed and measured.

Stopper end 44 and piston 22 both provide means for varying the size of samples. In fact, an advantage of the invention is that sample sizes may be easily varied. Sampling tube 18 may be made different sizes and shapes. Also, for a given size of sample tube 18, the travel of piston 22 may be adjusted so that stopper end 44 is located according to the retracted cycle of piston 22, and different amounts of samples are contained within sample tube 18.

Sensor 20 communicates with sample tube 18 between port end 42 and stopper end 44. Sensor 20 comprises any sensor capable of measuring the physical properties of interest in removed product samples while the product samples are within sample tube 18. Examples of sample physical properties that could be measured with an appropriate sensor 20 are: (1) dielectric constant (e.g., electrical capacitance in the frequencies from 700 Hz to several MHz); (2) microwave absorption (e.g., X-band (10 GHz) absorption); (3) electrical resistance (both dc and ac); (4) infrared absorption (e.g., wavelengths of several microns); or (5) hydrogen transient nuclear magnetic resonance (HTNMR).

In a preferred embodiment, sensor 20 comprises an HTNMR sensor. In this example, the HTNMR sensor further comprises magnet 15 and radio frequency coil 17 for producing a quadrature pair of magnetic fields. The quadrature pair of magnetic fields comprises a fixed bias field that magnet 15 produces and a radio frequency field that radio frequency coil 17 produces.

Magnet 15 may be any one of a number of devices for producing a magnetic field, including a permanent magnet or electromagnet. In HTNMR sensor 20, the fixed bias field has variable strength, and the radio frequency field has variable frequency. HTNMR sensor 20 permits variations in these parameters for inducing nuclear magnetic resonance by product sample hydrogen molecules. The physical changes that result from nuclear magnetic resonance of the product sample relate directly to physical properties of the product sample. Known HTNMR techniques are available to convert data from HTNMR sensor 20 into useful product sample information.

The HTNMR sensor 20 of FIG. 2 is capable of sensing data for measuring the following product sample properties: (1) $T_1$ (spin-lattice relaxation time), which characterizes the time required to polarize the sample in a magnetic field prior to measurement; (2) $T_2$ (spin-spin relaxation time), which characterizes the effect on the measured nuclei of interaction with other nuclei of the same species; and (3) free induction decay (FID) signal, which provides the basic HTNMR signal amplitude. To avoid electronic interference in the 9-10 MHz range from computers and other systems in the industrial environment, for example, an HTNMR sensor operating frequency of 11 MHz is preferable. These choices of parameters and frequency offer a good compromise between small, low-cost sensors, rejection of interference and good signal-to-noise ratios. Following these guidelines, sensor 20 comfortably accommodates the 1.5" internal diameter of the preferred embodiment for sampling tube 18 and can be designed to use a permanent magnet, thereby, further lowering operating costs and reducing system complexity.

Because sensor 20 fits completely within housing 16 and does not contact the product sample, sensor 20 can easily provide real-time, on-line measurements by a system that is sufficiently robust to withstand a variety of harsh industrial environments. Moreover, this design should provide an on-line product sampling apparatus having high reliability in terms of long mean time between failure, low operating costs and a suitable price-to-performance ratio. These qualities should make such a system economically attractive for industrial implementation. Such a system also can be made very compact, thus permitting great flexibility in locating sensors compared to those using separate measurement means or product thief streams.

Piston 22 provides a means for transferring product samples from flow line 14 through sampling aperture 11 to the sample tube 18 and for returning product samples to flow line 14 through sampling aperture 11 after sensor 20 senses the properties of interest. Piston 22 fits within sample tube bore 40 and is mounted to reciprocate between port end 42 and stopper end 44 of sample tube 18. Thus, in a preferred embodiment, the movement of piston 22 from port end 42 to stopper end 44 develops a suction force, which causes product to exit flow line 14 through sampling aperture 11 and to enter sample tube 18. As piston 22 moves from stopper end 44 to port end 42, piston 22 exerts positive pressure to cause the product sample to exit sample tube 18 through sampling aperture 11 to return to flow line 14. In a preferred embodiment, piston 22 engages sampling aperture 11 to seal sample tube 18 from the product stream 12 in flow line 14 when piston 22 is positioned at port end 42. This prevents leakage between flow line 14 and sample tube 18 when measurements are not being made.

The forces that cause a product sample to enter sample tube 18 may be a pressure differential that piston 22 creates by changing position between port end 42 and stopper end 44, gravitational force that the product stream experiences, or a combination of a pressure differential and gravitational forces. The particular combination of forces that cause product to enter sample tube 18 depend upon the relative configurations of flow line 14 and sample tube 18.

In addition to the advantages described above, the configuration of the preferred embodiment has several more advantages over known systems. For example, by returning the product sample to the product stream 12, the invention eliminates product wastage and the need for a means to dispose of the sampled product. Also, if the viscosity of the product stream 12 is sufficiently low (i.e., low viscosity liquids, gases or fine particles), piston 22 can be designed with a very small diameter. This would reduce the size and costs of the magnet system and radio frequency amplifiers required to perform HTNMR, for example. Additionally, the apparatus of the present invention allows measurement of samples in a static (non-flowing) state. The length of time during which the product sample remains within sample tube 18 may be adjusted as desired. This permits the use of more time-consuming sensor measurements, if desired.

Figure 3C:
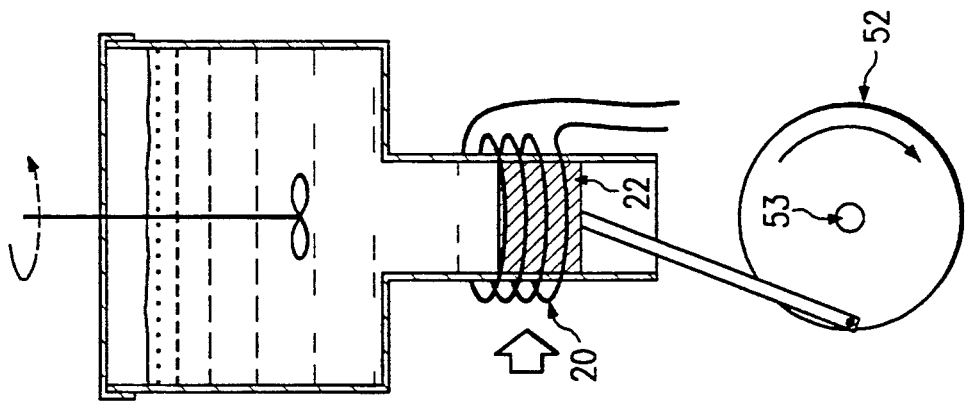
FIGS. 3a through 3c are a series of schematic side elevational views of a preferred embodiment of the apparatus showing rotation of the actuator and reciprocation of the piston to repeatedly fill and then empty the sample tube.
Figure 3B:
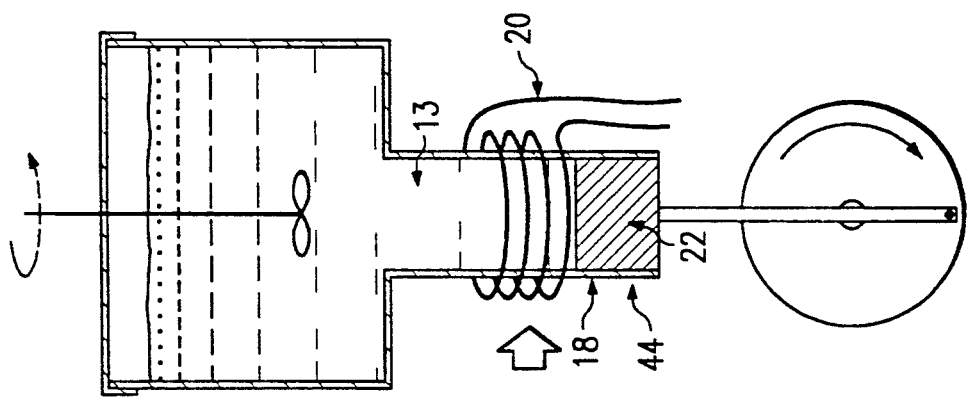
Figure 3A:
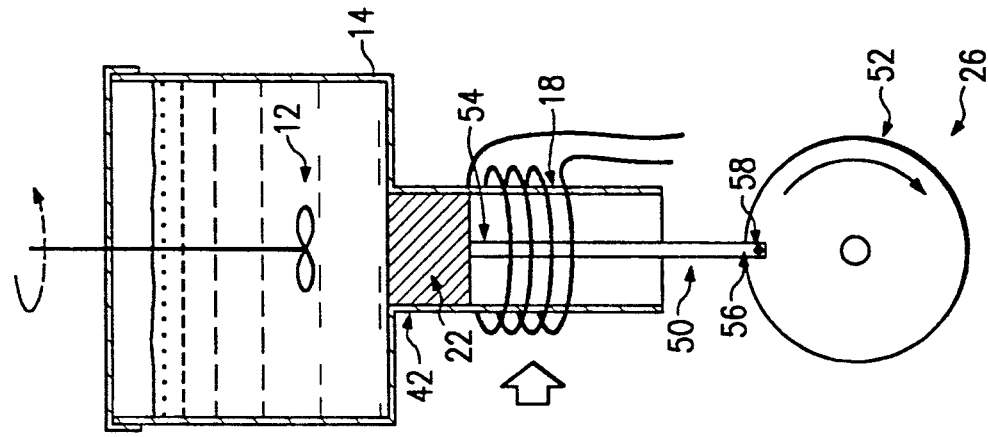

FIGS. 3a through 3c are a series of schematic side elevational views of a preferred embodiment of sampler 10 showing rotation of actuator 26 and reciprocation of piston 22 to fill and then empty sample tube 18. Actuator 26 is connected to piston 22 to reciprocate piston 22 between sample tube port end 42 and stopper end 44. In the embodiment of FIGS. 3a through 3c, actuator 26 comprises shaft 50 and rotating wheel 52. Shaft 50 has a piston end 54 and a wheel end 56. Shaft 50 pivotally engages piston 22 at piston end 54 and the outer rim 58 of the rotating wheel 52 at wheel end 56. Thus, as wheel 52 rotates, shaft 50 causes piston 22 to reciprocate between port end 42 and stopper end 44 of sample tube 18.

A sampling sequence could begin, for example, with piston 22 at port end 42 and wheel end 56 of shaft 50, engaging outer rim 58 at a point close to sample tube 18 (FIG. 3a). With piston 22 at port end 42, in a preferred embodiment, piston 22 seals product stream 12 in flow line 14 from sample tube 18. FIG. 3b shows piston 22 fully drawn into sample tube 18 at stopper end 44. At this point, product sample 13 fills sample tube 18.

Once product sample 13 enters sample tube 18, sensor 20 may then sense product sample physical properties of interest. The reciprocating path of piston 22 that wheel 52 creates by its rotating about axis 53 appears in FIG. 3c. Reciprocation of piston 22 will continue throughout the rotation of wheel 52. Also, during the reciprocating movement, piston 22 passes sensor 20. In one embodiment of the invention, as mentioned above, a calibration means (not shown) could be included in piston 22. As piston 22 proceeds along its path, sensor 20 could measure the calibration means for purposes of either real-time or subsequent calibration of sensor 20 data.

In yet another embodiment of the invention, actuator 26 could remain stationary for a desired period of time when piston 22 is at stopper end 44. This would allow the product sample to sit in sample tube 18 for that period of time for various measurements. For example, a product sample could remain in sample tube 18 for a time sufficient to allow the separation of various phases. Thus, air bubbles could be separated out of the product sample, or solids might fall out of suspension, thereby permitting separate measurements of solid, liquid and gaseous components.

Figure 4:
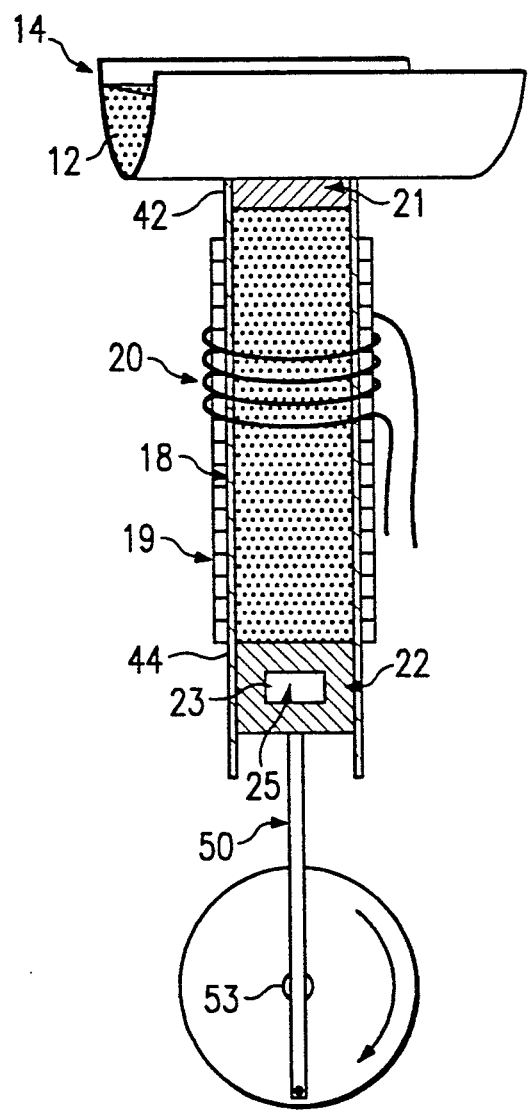
FIG. 4 is a schematic side view of an alternative embodiment of the invention.

FIG. 4 schematically shows several alternative features of the invention. In this example, if piston 22 is fabricated in the form of a cylinder of some nonconductive medium (e.g., Teflon, ceramic, glass or, in the case that the HTNMR nucleus of interest is not hydrogen, any of a number of plastics), it would be possible to form a sealed hollow cavity 23 within piston 22. Cavity 23 could be filled with material 25 having known physical properties. As this calibration standard material 25 passes sensor 20, sensor 20 measures its properties. The measurement could be used to calibrate the apparatus, provide tuning adjustments, or adjust temperatures, for example. Also, a number of cavities 23 inside piston 22 could provide additional calibration measurements. This would greatly increase the accuracy and utility of the apparatus.

FIG. 4 also schematically shows alternative embodiments of sampling tube 18, which further comprise temperature cycling means 19 and filter 21. Temperature cycling means 19, for example, surrounds sample tube 18 between port end 42 and stopper end 44. With product sample 13 in sample tube 18, temperature cycling means 19 raises the product sample temperature to a desired level and at a desired rate, depending on the product being sampled to permit tempering of the product sample 13 or other product sample phase modification. Filter 21 appears at port end 42 and provides a means for removing particulate contaminants from the sample being measured. Placement of filter 21 at port end 42, for example, ensures that sensor 20 more accurately measures product sample physical properties of interest.

Although the invention has been described with reference to the above specific embodiments, this description is not meant to be construed in a limiting sense. Various modifications of the disclosed embodiment, as well as alternative embodiments of the invention will become apparent to persons skilled in the art upon reference to the above description. It is therefore contemplated that the appended claims will cover such modifications that fall within the true scope of the invention.

What is claimed is:

1. An on-line product sampling apparatus for measuring product samples from a product stream in a flow line having a sampling aperture, comprising:
   a sampling tube for attachment under a flow line, such that it receives product samples via and aperture in said flow line, said sampling tube having an open port end in communication with said aperture, and said sample tube having an open stopper end opposite said port end;
   a piston moveable within said sampling tube, having a substantially sealed relationship to the inner walls of said sampling tube such that said piston may be moved upwardly within said sampling tube to provide an upward force at the bottom surface of said sample to return said sample to said product stream via said aperture;
   a sensor in communication with said sampling tube for sensing physical properties of said sample while said sample is within said sample tube; and
   wherein said piston further comprises a hollow piston head for containing material for calibrating said sensor.

2. A method for sampling and measuring product samples from a product stream in a flow line, comprising the steps of:
   receiving a product sample, from the flow line through an aperture in said flow line into a sample tube, such that a sample having a finite static quantity enters said sample tube;
   moving a piston, having a substantially sealed relationship with said sample tube, within said sample tube away from said aperture, while said sample enters said sample tube;
   containing said sample within said sample tube, said sample tube being in direct communication with the flow line at said aperture;
   sensing physical properties of said sample while said sample is stationary within said sample tube;
   returning all of said sample to said flow line through said aperture by moving a piston toward said aperture from behind said sample tube such that said piston does not enter said flow line; and
   wherein said steps of receiving, containing, sensing, and returning occur such that a near real-time measurement of said physical properties of product at a known point in said flow line is obtained.

3. The method of claim 2, further comprising the step of filtering the product samples as the product samples pass from the flow line through the sampling aperture to the sample tube.

4. The method of claim 2, wherein said sensing step comprises sensing physical properties of removed product samples with a nuclear magnetic resonance sensor while the product samples are stationary within said sample tube.

5. The method of claim 4, and further comprising the step of timing said nuclear magnetic resonance measurements to obtain spin relaxation time data.

6. The method of claim 2, and further comprising the step of adjusting the travel of said piston to alter the size of said samples.

7. The method of claim 2, wherein said steps are repeated in a periodic cycle, such that a series of near real-time measurements are obtained.

8. The method of claim 2, wherein said containing step occurs for a predetermined time while said piston remains in a retracted position.

9. The method of claim 2, and further comprising the step of changing the temperature of said sample during said containing step.

* * * * *